United States Patent
Adams

(10) Patent No.: US 7,819,848 B2
(45) Date of Patent: Oct. 26, 2010

(54) SYSTEMS AND METHODS FOR FLUSHING CATHETERS

(75) Inventor: Craig L. Adams, Dublin, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1141 days.

(21) Appl. No.: 10/794,039

(22) Filed: Mar. 4, 2004

(65) Prior Publication Data

US 2004/0171937 A1   Sep. 2, 2004

Related U.S. Application Data

(62) Division of application No. 10/253,392, filed on Sep. 23, 2002, now abandoned.

(51) Int. Cl.
*A61M 5/14* (2006.01)

(52) U.S. Cl. .................. 604/256; 604/129; 604/167.01

(58) Field of Classification Search ................ 604/523, 604/288.02, 122, 124, 125, 129, 35, 256, 604/411, 167.01
See application file for complete search history.

(56) References Cited

U.S. PATENT DOCUMENTS

| | | | |
|---|---|---|---|
| 3,122,136 A | | 2/1964 | Murphy, Jr. |
| 3,586,064 A | | 6/1971 | Brown et al. |
| 4,245,636 A | | 1/1981 | Sparks et al. |
| 4,593,973 A | | 6/1986 | Yoshida et al. |
| 4,624,662 A | | 11/1986 | Le |
| 4,714,461 A | | 12/1987 | Gabel |
| 4,790,315 A | | 12/1988 | Mueller et al. |
| 4,811,737 A | * | 3/1989 | Rydell ........................ 606/194 |
| 4,850,969 A | * | 7/1989 | Jackson ................... 604/96.01 |
| 5,002,059 A | | 3/1991 | Crowley et al. |
| 5,135,486 A | * | 8/1992 | Eberle et al. ............. 604/103.1 |
| 5,357,961 A | | 10/1994 | Fields et al. |
| 5,372,138 A | | 12/1994 | Crowley et al. |
| 5,523,092 A | | 6/1996 | Hanson et al. |
| 5,549,548 A | | 8/1996 | Larsson |
| 5,752,970 A | * | 5/1998 | Yoon ........................... 606/185 |
| 5,797,888 A | * | 8/1998 | Yoon ........................... 604/530 |
| 5,823,961 A | | 10/1998 | Fields et al. |
| 6,074,362 A | * | 6/2000 | Jang et al. .................... 604/104 |
| 6,113,938 A | | 9/2000 | Chen et al. |
| 6,117,102 A | | 9/2000 | Schwartz et al. |
| 6,217,557 B1 | * | 4/2001 | Hakansson et al. ...... 604/167.06 |
| 6,416,510 B1 | | 7/2002 | Altman et al. |
| 2004/0059228 A1 | * | 3/2004 | Wasicek et al. ............. 600/466 |

* cited by examiner

*Primary Examiner*—Nicholas D Lucchesi
*Assistant Examiner*—Quynh-Nhu H Vu
(74) *Attorney, Agent, or Firm*—Frommer Lawrence & Haug LLP; Bruce E. Black

(57) ABSTRACT

Various improvements are made to catheters adapted to be flushed to remove air from within the catheter. For example, improved catheters include a catheter with a self-sealing seal at its distal end to pass a venting tube for removing air from within the catheter, a catheter having a distal end whose diameter is reduced to compress a seal adapted to pass a venting tube; a catheter having a cap at its distal end where the cap has a venting hole that is opened or closed depending on the conditions subjected to the shape-memory material of the cap; a catheter having a vent hole at its distal end; a catheter having an opening at its distal end that can be closed by a plug; and a catheter having a narrow neck with an opening to vent air and the neck is coupled to a tab where twisting the tab closes the opening in the neck.

15 Claims, 10 Drawing Sheets

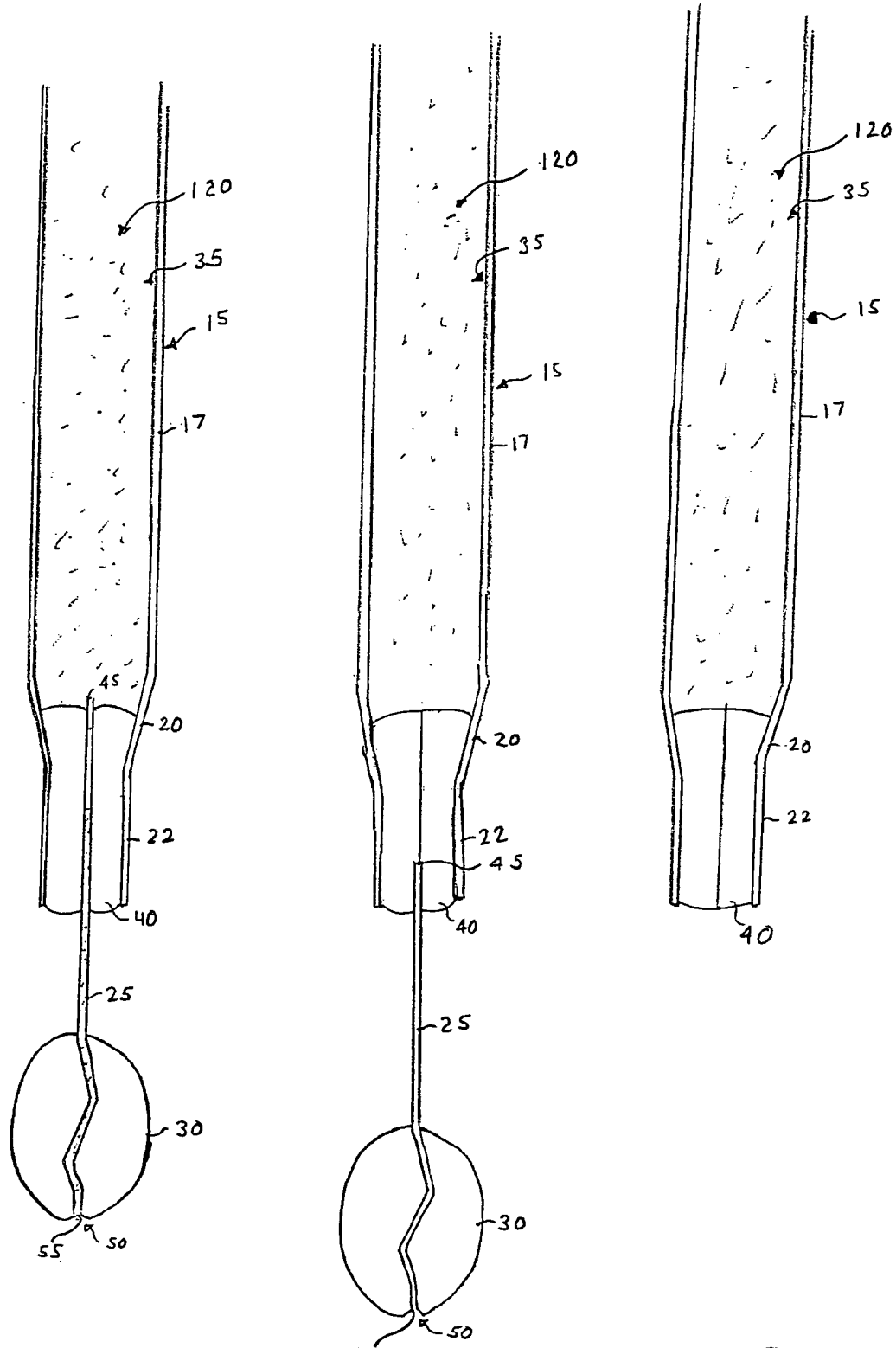

SYSTEMS AND METHODS FOR FLUSHING CATHETERS

CROSS REFERENCE TO RELATED APPLICATIONS

This application is a divisional of application Ser. No. 10/253,392, filed Sep. 23, 2002, now abandoned which is fully incorporated herein by reference.

BACKGROUND OF THE INVENTION

1. Field of the Invention

The field of the invention relates to prepping catheters, and more particularly to flushing catheters.

2. Background

Catheters are commonly used to access the interior of a patient's body. The distal end of the catheter may be equipped with a medical device, e.g., an ultrasound transducer, a light imaging device, a balloon, or the like, for performing medical procedures in the body. Alternatively or in addition, the distal end of the catheter may have an opening for releasing therapeutic agents in the body. To access a treatment site in the body, the catheter is advanced through a body lumen, e.g., blood vessel, to the treatment site.

Catheters include an elongated catheter body having one or more lumens extending through the catheter body. A medical device, e.g., an ultrasound transducer, may be slideable received within the catheter body lumen. Prior to use in a medical procedure, the catheter body lumen is flushed with a flushing solution, such as saline or sterile water. The solution displaces the air in the catheter lumen, thereby reducing the risk of air being accidentally released in the body from the catheter. In addition, for a catheter comprising an ultrasound transducer, the solution provides an acoustic coupling media for coupling ultrasound energy between the ultrasound transducer and the surrounding body.

Prior to use, a physician or nurse removes the catheter from a sealed package in a sterile environment. The physician then preps the catheter for insertion into the patient's body. The prepping procedure includes flushing the catheter lumen with flushing solution, e.g., saline or sterile water, to remove air from the catheter lumen. This may be done, e.g., by inserting a syringe 75 filled with the flushing solution into a valve 70 coupled to the proximal end of the catheter 65 and injecting the solution into the catheter lumen through the valve 70, as illustrated in FIG. 23.

Even though the catheter lumen is flushed with the flushing solution, air bubbles may remain trapped in the catheter. To address this problem, several techniques have been developed to remove air bubbles from the catheter. One technique is to hold the catheter at a distance from its distal tip and swirl the catheter. Swirling the catheter produces a centrifugal force that pulls the solution towards the distal end of the catheter, displacing trapped air bubbles. A problem with this technique is that the physician or nurse swirling the catheter may accidentally strike a nearby object, e.g., medical equipment or table, with the catheter, damaging the catheter.

Another technique is to provide a self-sealing septum at the distal end of the catheter. In this technique, flushing solution is injected into the catheter lumen from the distal end rather than the proximal end of the catheter. A syringe filled with the flushing solution is inserted into the distal end of the catheter through the self-sealing septum and the solution is injected into the catheter lumen. The syringe is then pulled out of the septum, and the septum seals itself. A problem with this technique is that the physician or nurse inserting the syringe into the distal end of the catheter may accidentally puncture the side wall of the catheter or damage a medical device in the catheter with the needle tip of the syringe.

Therefore, there is a need for an improved system and method for flushing catheters.

SUMMARY OF THE INVENTION

Various improvements are made to catheters adapted to be flushed to remove air from within the catheter. Example improvements include, but are not limited to, a catheter having a self-sealing seal at its distal end to pass a venting tube for removing air from within the catheter; a catheter having a distal end whose diameter is reduced to compress a seal adapted to pass a venting tube; a catheter having a cap at its distal end where the cap has a venting hole that is opened or closed depending on the conditions subjected to the shape-memory material of the cap; a catheter having a vent hole at its distal end; a catheter having an opening at its distal end that can be closed by a plug; and a catheter having a narrow neck with an opening to vent air and the neck is coupled to a tab where twisting the tab closes the opening in the neck.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the concepts being discussed. All illustrations are intended to convey concepts, where relative sizes, shapes and other detailed attributes may be illustrated schematically rather than literally or precisely. Moreover, in the figures, like reference numerals designate corresponding parts throughout the different views. However, like parts do not always have like reference numerals.

FIG. 7 illustrates the catheter of FIG. 1B filled with flushing solution.

FIG. 8 illustrates the hypo tube partially removed from the soft seal.

FIG. 9 illustrates the catheter after removal of the hypo tube from the soft seal.

DETAILED DESCRIPTION OF THE PREFERRED EMBODIMENTS

Figure 1A:
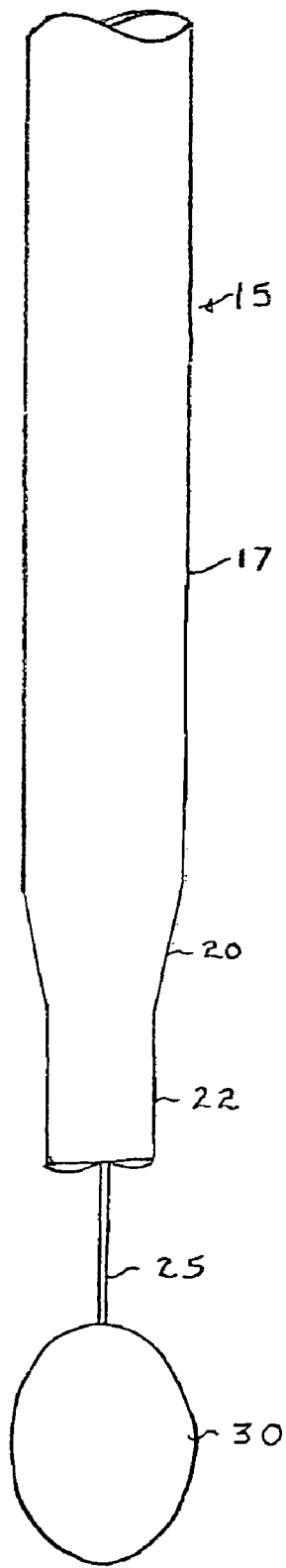
FIG. 1A is a top view of an air-venting apparatus of an improved catheter.
Figure 1B:
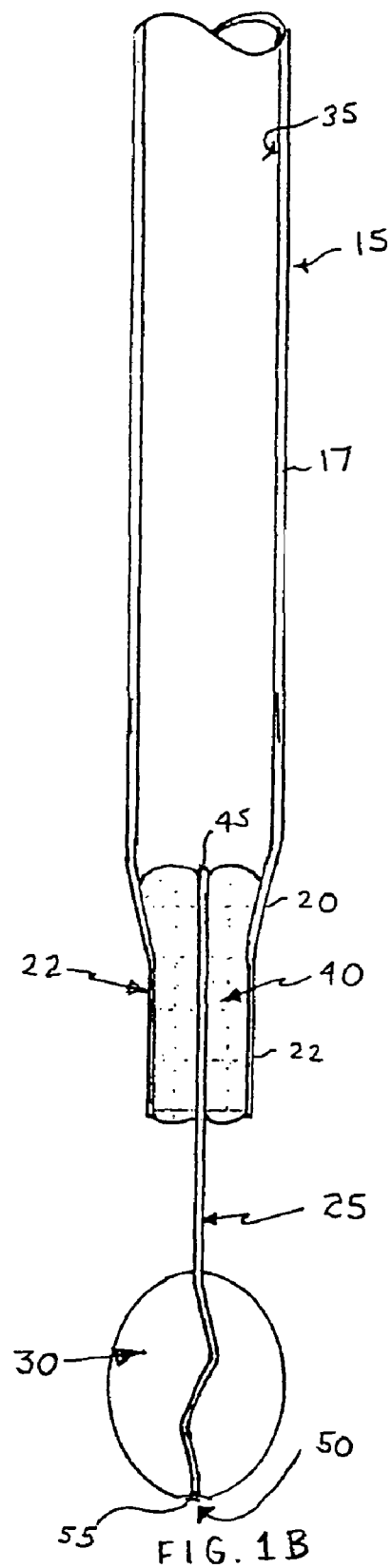
FIG. 1B is a cross-sectional top view of an air-venting apparatus of the improved catheter of FIG. 1A.

An example embodiment of an improved catheter with an air-venting apparatus is illustrated in FIG. 1A (top view) and FIG. 1B (cross-sectional top view). The catheter includes an elongated catheter body 15 having a lumen 35 extending through the catheter body. Suitable materials for the catheter body 15 include Pebax 70A, Tecoflex, Polyethelene, Nylon, rubber, thermoplastic polymers and other materials. The catheter body 15 preferably includes a main portion 17, a distal portion 22 having a smaller diameter than the main portion 17, and a tapered portion 20 that tapers downward from the main portion 17 to the distal portion 22. The main portion 17 of the catheter body 15 may have a diameter of, e.g., 0.020-0.120 inches and the distal portion 22 may have a diameter of, e.g., 0.01 to 0.12 inches (4 to 6 French). The lumen 35 in the main portion 17 of the catheter body 15 may slideably receive an ultrasound transducer, a light imaging device (e.g., OCT, OCDR, etc), or other medical device (not shown).

The air-venting apparatus includes a soft seal 40 in the catheter lumen 35 at the distal portion 22 of the catheter body 15. The soft seal 40 is preferably made of an elastic shape-memory material that is able to recover its original shape from a deformed state when a force deforming the material is removed. Suitable shape-memory materials include Pebax 35D, silicone, and the like. The venting apparatus further includes a hypo tube 25 extending through the soft seal 40. Preferably, the hypo tube 25 is made of a durable material, such as stainless steel or plastic. The hypo tube 40 may have an outer diameter of, e.g., 0.009 inches, and an inner diameter of, e.g., 0.004 inches. The hypo tube 25 also includes a distal portion extending outwardly from the catheter body 15. The hypo tube 25 is used to provide an opening through the seal 40 for venting air from the catheter lumen 35 to the outside in a flushing procedure, as explained further below.

The air-venting apparatus preferably includes a pull tab 30 attached to the distal portion of the hypo tube 25. The pull tab 30, which may be made of plastic or metal, provides a gripping surface for pulling the hypo tube 25 out of the soft seal 40. Alternatively, the pull tab 30 may be omitted and the hypo tube 25 may be pulled out of the soft seal 40 by gripping the hypo tube 25 with a gripping instrument, such as a hemostat, tweezers, and the like. In this case, the outer surface of the hypo tube 25 may be roughened, e.g., by sand blasting the surface, to enable the gripping instrument to obtain a tighter grip on the hypo tube 25.

In the embodiment illustrated in FIG. 1B, the distal portion of the hypo tube 25 has a zigzag shape, which mechanically secures the hypo tube 25 to the pull tab 30 by preventing the pull tab 30 from sliding off of the hypo tube 40. Of course, other geometries besides a zigzag shape may be used. Alternatively or in addition, the hypo tube 25 may be secured to the pull tab 30 by an adhesive, weld, or other known securing means. In this case, the outer surface of the hypo tube 25 may be roughened to enable the adhesive to better adhere to the hypo tube 25. The hypo tube 25 may also be encased in the pull tab 30 by placing the hypo tube 40 in a mold and injecting injection molding plastic into the mold to form the pull tab 30.

In the embodiment illustrated in FIG. 1B, the pull tab 30 further includes a notch 50. The distal tip 55 of the hypo tube 25 terminates at the bottom of the notch 50, thereby recessing the distal tip 55 in the pull tab 30. This prevents the distal tip 55 of the hypo tube 25 from accidentally puncturing a package (not shown) in which the catheter 12 is sealed prior to use. Alternatively, a removable cap may be fitted onto the distal tip 55 of the hypo tube 40 to prevent the distal tip 55 from puncturing the package.

Figure 2:
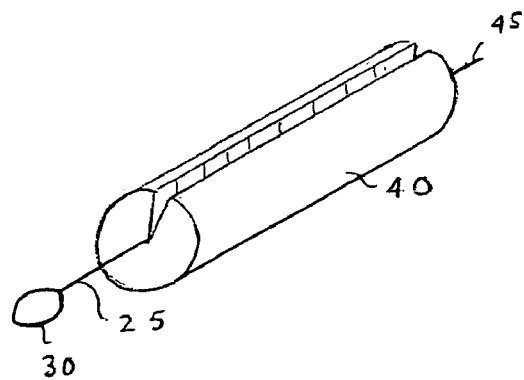
FIG. 2 illustrates a soft seal that is sliced along the longitudinal direction for placement of a hypo tube through the seal.
Figure 3:
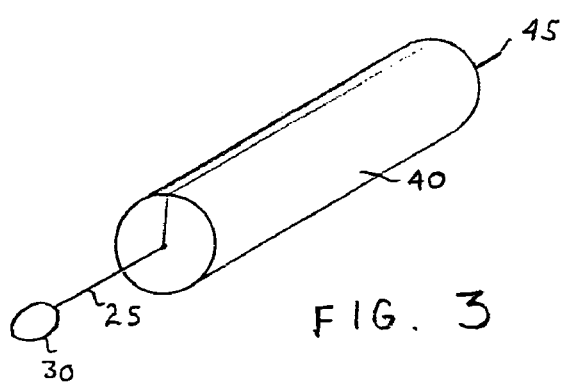
FIG. 3 illustrates the soft seal closed around the hypo tube.
Figure 4:
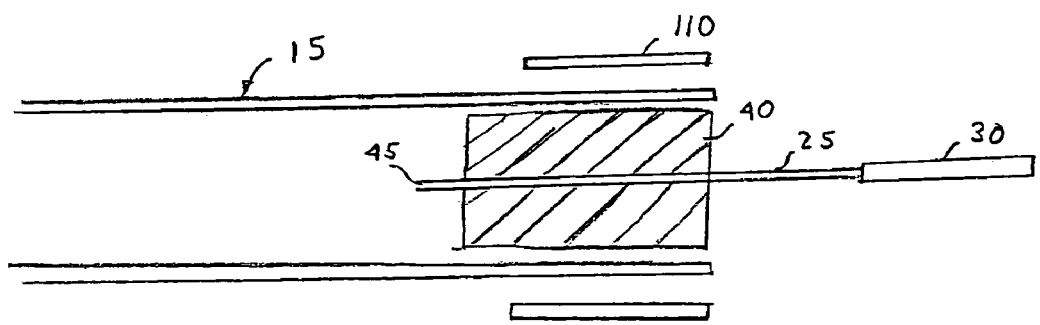
FIG. 4 illustrates the soft seal and hypo tube inserted into a catheter body.
Figure 5:
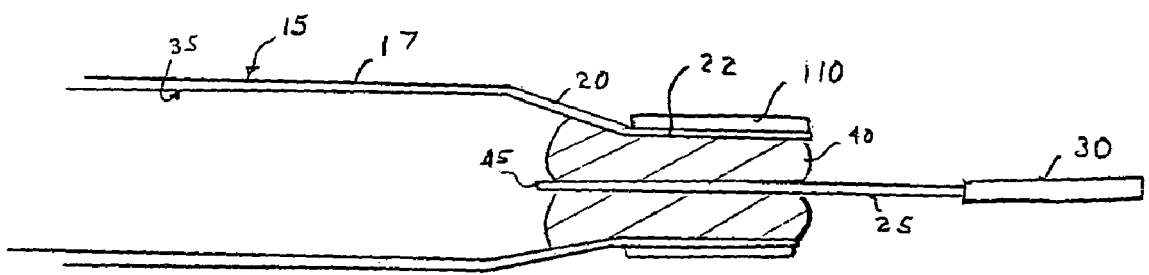
FIG. 5 illustrates the catheter body compressed around the soft seal by a heat shrink.
Figure 6:
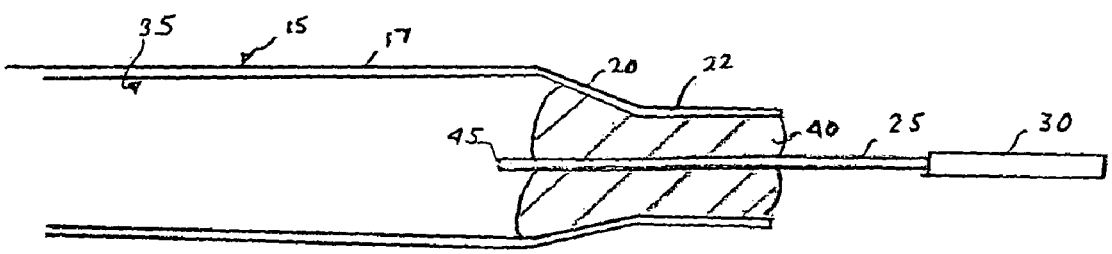
FIG. 6 illustrates the catheter body compressed around the soft seal after the heat shrink is removed.

An example embodiment of a method for fabricating and fitting the venting apparatus in the catheter body 15 will be described with reference to FIGS. 2 through 6. In FIG. 2, the soft seal 40 initially has a cylindrical shape having a diameter between that of the main portion 17 and the distal portion 22 of the catheter body 15. The soft seal 40 is then sliced along the longitudinal direction to the center of the seal 40. The hypo tube 40 is laid along the centerline of the soft seal 40 such that the proximal end 45 of the hypo tube 25 extends past the soft seal 40. In FIG. 3, the soft seal 40 closes around the hypo tube 25 due to the shape-memory property of the soft seal 40 material. In FIG. 4 (cross-sectional side view), the soft seal 40 is inserted into the catheter lumen 35 from a distal opening of the catheter body 15. Initially, the catheter body 15 has a uniform diameter. A cylindrical heat shrink sleeve 110 is positioned around the catheter body 15 and the soft seal 40. The heat shrink 110 may be made of RNF, Polyester, or the like. The proximal end 42 of the soft seal 40 extends past the heat shrink 110. In FIG. 5, heat is applied to the heat shrink 110, e.g., by blowing hot air on the heat shrink 110. The heat causes the heat shrink 110 to shrink around the underlying catheter 15 and compress the underlying catheter body 15 to a smaller diameter. In addition, some of the heat transfers from heat shrink 110 to the underlying catheter body 15, softening the underlying catheter body 15 and making it easier to reshape. The combination of compression and heat from the heat shrink 110 reshapes the underlying catheter body 15 to form the distal portion 22 of the catheter body 15. Furthermore, the compression of the catheter body 15 around the soft seal 40 firmly fits the soft seal 40 in the catheter body 15. After the heat shrink 110 cools, the underlying catheter body 15 hardens and maintains its compressed shape when the heat shrink 110 is removed, as shown in FIG. 6. The heat shrink 110 may be removed by cutting a slit in the heat shrink 110 and peeling away the heat shrink 110. Even though a heat shrink was used to reshape the distal end of the catheter body 15 in the just-described embodiment, those skilled in the art will appreciate that other methods may be used, such as crimping and heating the catheter body 15 with heat crimpers.

Figure 23:
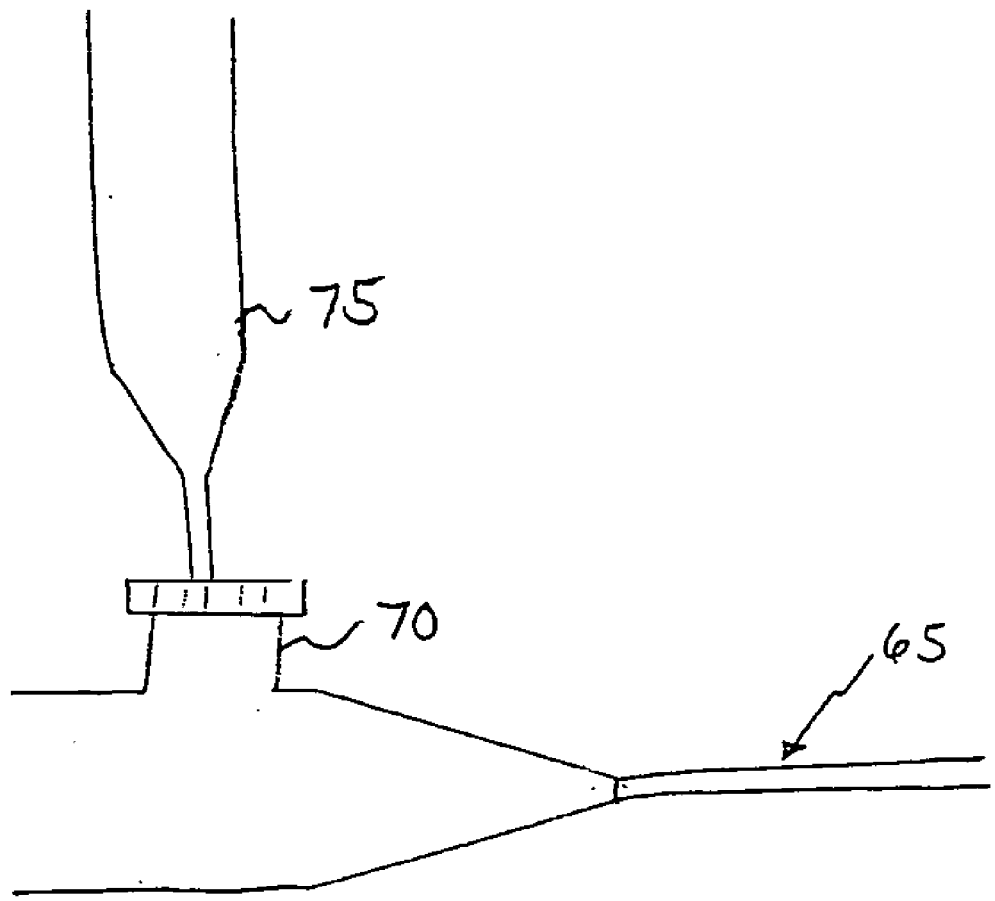
FIG. 23 shows a syringe filled with flushing solution inserted into a valve coupled to the proximal end of a prior art catheter.

The operation of the example embodiment of the venting apparatus will now be described with reference to FIGS. 7 to 9 (all cross-sectional top views). The catheter lumen 35 is flushed with flushing solution, e.g., saline or sterile water, from the proximal end (not shown) of the catheter body 15. The injection of flushing solution may be accomplished using any method used for prior art catheters such as that in FIG. 23. The flushing solution flows to the distal end of the catheter lumen 35, where it forces air in the lumen 35 to vent out through the hypo tube 25 to the outside. Eventually, the solution fills the catheter lumen 35 and slowly leaks out through hypo tube 25 at a drip rate due to the capillary forces of the solution in the hypo tube 25. FIG. 7 illustrates the catheter lumen 35 filled with the flushing solution 120. The hypo tube 25 is then slowly pulled out of the soft seal 40 by pulling on the pull tab 30. Preferably, the hypo tube 25 is pulled out slowing so that any residual air bubbles that may be trapped between proximal end 45 of the hypo tube 25 and the soft seal 40 will be evacuated out of the lumen 35 through the hypo tube 25 as it is pulled out. As the hypo tube 25 is removed from the soft seal 40, the seal 40 closes over the hypo tube 25, as illustrated in FIG. 8. This is possible because of the shape-memory property of the soft seal 40 material, which attempts to recover its original shape by filling the void left by the removal of the hypo tube 25. FIG. 9 illustrates the soft seal 40 after removal of the hypo tube 25. The soft seal 40 seals itself, thereby sealing off the distal end of the catheter lumen 35 and retaining the flushing solution 120 in the catheter lumen 35.

Figure 10:
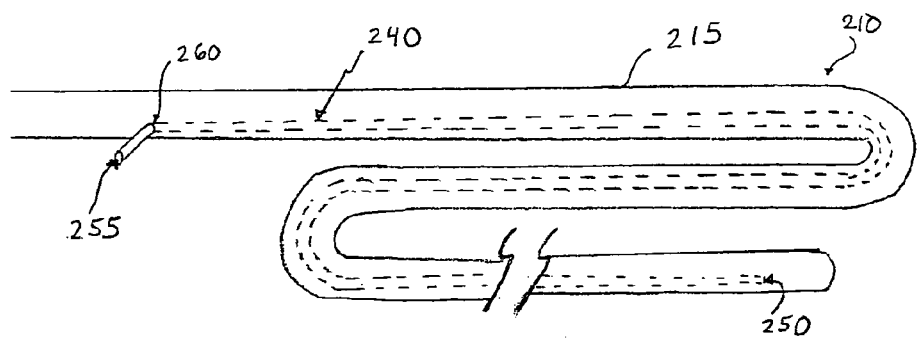
FIG. 10 is perspective view of a hypo tube extending through a lumen of an improved catheter.
Figure 11:
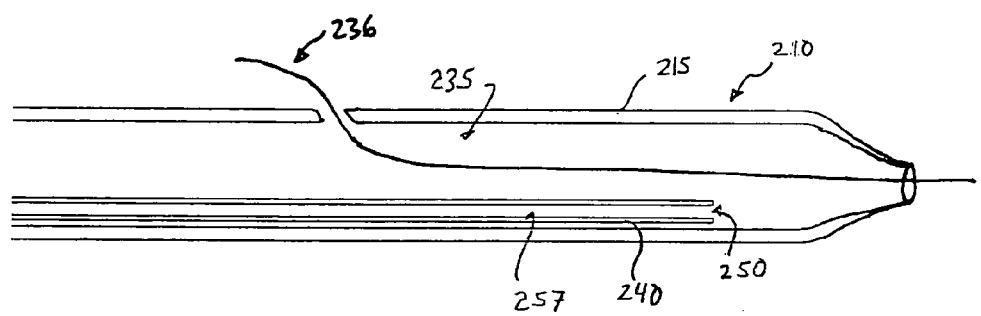
FIG. 11 is a cross-sectional view of the catheter lumen and hypo tube of FIG. 10.

Another embodiment of a catheter with an air-venting apparatus is illustrated in FIG. 10 (perspective view) and FIG. 11 (cross-sectional view). The catheter 210 includes an elongated catheter body 215 having a lumen 235 extending through the catheter body 215. The air-venting apparatus preferably comprises a hypo tube 240 within the catheter lumen 235 extending from a distal portion of the catheter 210 to a proximal portion of the catheter 210. A portion of the hypo tube 240 protrudes out of the catheter 210 through an exit hole 260 on the side of the catheter 210. The exit hole 260 is preferably located on a portion of catheter 210 that will not be inserted into the patient's body during a medical procedure.

The hypo tube 240 has an inlet 250 located at the distal portion of the catheter 210 and an outlet 255 located outside of the catheter 210. The inlet 250 and outlet 255 are coupled by a lumen 257 extending through the hypo tube 240. The hypo tube 240 may be made of, but is not limited to, polymide (PI), stainless steel, polymer, nylon, or a combination thereof. The hypo tube 240 may have an outer diameter of 0.005 to 0.02 inches and an inner diameter defined by the lumen of 0.0015 to 0.018 inches.

Figure 12:
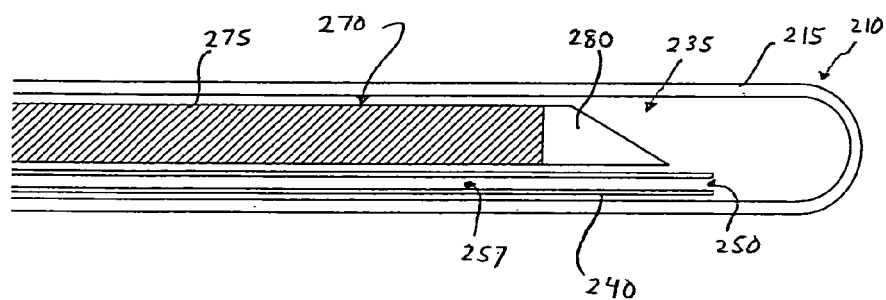
FIG. 12 is a cross-sectional view of the catheter lumen of FIG. 11 further including an imaging core within the catheter lumen.

A medical device may be placed within the catheter lumen 235 alongside the hypo tube 240. For example, FIG. 11 shows a guidewire 236 and FIG. 12 shows an imaging core 270 within the catheter lumen 235 comprising a transducer 280 coupled to a drive shaft 275. In this example, the hypo tube 240 is between the imaging core 270 and the inner surface of the catheter lumen 235. The outer diameter of the hypo tube 240 is less than the difference between the diameter of the catheter lumen 235 and the outer diameter of the imaging core 270. The medical device can be any medical device adapted for use in a catheter and may be used with any of the catheter embodiments described in this specification. Such medical devices include, but are not limited to, ultrasound imaging devices, light imaging devices, cutting tools (assumes that the catheter has an opening at its distal end), drug releasing devices, guidewires, etc.

To flush the catheter 210, a flushing solution is injected into the catheter lumen 235 from the proximal end of the catheter 210. The flushing solution reaches the distal end of the catheter lumen 235 and flows into the hypo tube lumen 257 through the inlet 250. As the solution flows into the hypo tube lumen 257, it pushes air from the catheter lumen 235 through the hypo tube lumen 257. The air is then vented to the outside from the outlet 255 of the hypo tube 240. The advantage of the hypo tube 240 according to this embodiment is that it vents air from the catheter lumen 235 without the need for vent holes at the distal end of the catheter 210. This reduces the risk of air bubbles being released into the body from the catheter during a medical procedure.

The hypo tube 240 is preferably removed from the catheter 210 after the flushing procedure by pulling the hypo tube 240 out through the exit hole 260. This leaves more space in the catheter lumen 235 to accommodate medical devices within the lumen. For the example of the imaging core 270 within the catheter lumen 235, the hypo tube 240 may be removed so it does not interfere with the operation of the imaging core 270 during a medical procedure. A valve connector may be used at exit hole 260 to prevent the flushing solution from leaking out of the exit hole.

Figure 13:
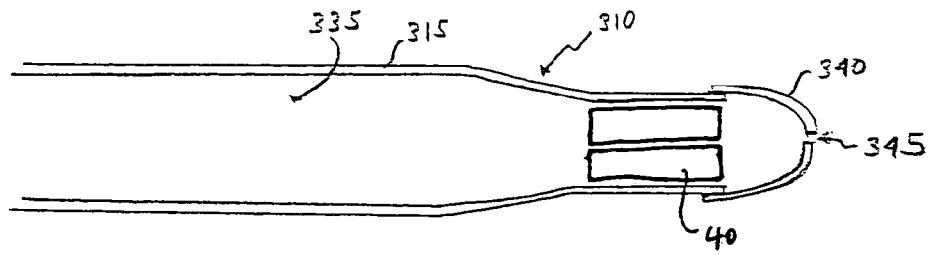
FIG. 13 is a cross-sectional view of another embodiment of an improved catheter comprising a distal cap having a self-sealing vent hole.

Another embodiment of a catheter with an air-venting apparatus is illustrated in FIG. 13 (cross-sectional view). The catheter 310 includes an elongated catheter body 315 having a lumen 335 extending through the catheter body. The catheter body 315 preferably tapers down to a smaller diameter at the distal end. The air-venting apparatus comprises an elastic cap 340 attached to the distal tip of the catheter body 315. The air-venting apparatus can also include an optional soft seal 40. The cap 340 has one or more seal-sealing vent holes 345 that self seals upon application of a stimulus, e.g., heat, pressure, or moisture, to the cap 340. The mechanism by which the vent hole 345 self seals is explained below.

Figure 14:
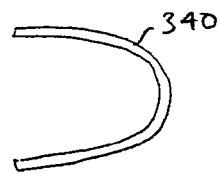
FIG. 14 is a cross-sectional view of the cap in its original shape.

An example embodiment of a method for fabricating the catheter will now be discussed with reference to FIGS. 14 and 15 (both cross-sectional views). FIG. 14 shows a cap 340 in its original shape made of an elastic shape-memory material that can be mechanically or otherwise deformed into a deformed shape. Once deformed, the shape-memory material maintains its deformed shape until a stimulus is applied to the material, upon which the material recovers its original shape. The stimulus may be heat, pressure, or moisture. Suitable shape-memory materials include, but are not limited to, hydrogels and shape-memory polymers. Shape-memory materials that are activated by heat or moisture include thermal plastic polymers or hydrophilic polymers. For example, thermally activated shape-memory materials may activate in a temperature range of 150-500 degrees Fahrenheit.

Figure 15:
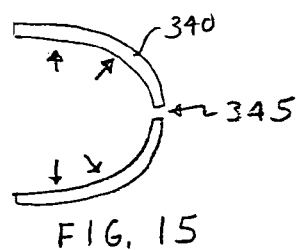
FIG. 15 is a cross-sectional view of the cap of FIG. 14 being stretched outwardly.

In the example illustrated in FIG. 15, the cap 340 is mechanically stretched outwardly (indicated by arrows) to a larger diameter, e.g., using a flaring tool. Once stretched, the cap 340 maintains its stretched shape until the stimulus, e.g., heat, pressure, or moisture, is applied to the cap 340. One or more vent holes 345 are bored through the cap 340. Even though the vent hole is shown in the center of the cap 340, the vent hole can be placed anywhere on the cap 340. The cap 340 is then attached to the distal tip of the catheter body 315 (not shown in FIG. 15), e.g., with an adhesive.

Figure 16:
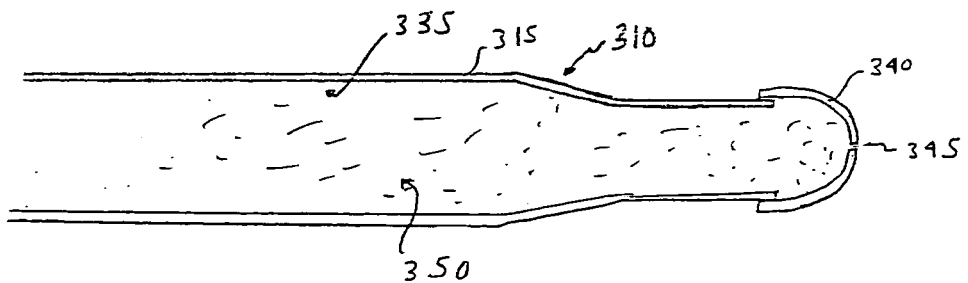
FIG. 16 is a cross-sectional view of the catheter of FIG. 13 in which the vent hole of the cap is sealed.

To flush the catheter, a flushing solution is injected into the catheter lumen 335 from the proximal end of the catheter 310. The solution flows to the distal end of the catheter lumen 335 where it pushes air out through the vent hole 345. After the air is vented out, the stimulus, e.g., heat, pressure, or moisture, is applied to the cap 340. When the stimulus is moisture, the moisture from the flushing solution may provide the stimulus. The stimulus activates the shape-memory material of the cap 340 causing the cap 340 to attempt to recover its smaller original shape. This in turn causes the vent hole 345 to shrink to a smaller diameter, thereby restricting the flow of flushing solution 350 though the vent hole 345, as illustrated in FIG. 16. The vent hole 345 may be dimensioned so that it closes to a diameter that allows little or no flushing solution 350 to flow through the vent hole 345 when the shape-memory material of the cap 340 is stimulated.

Figure 17:
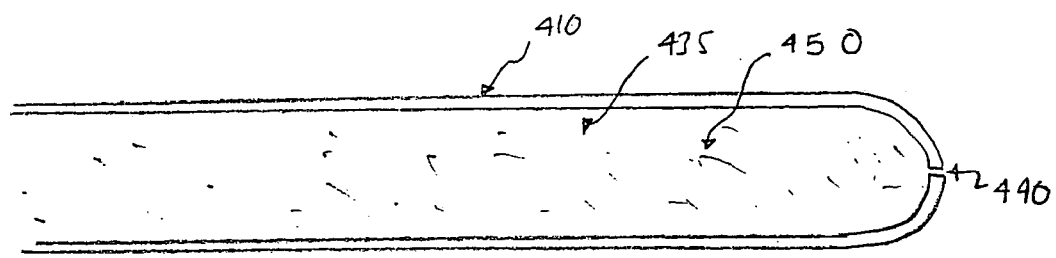
FIG. 17 is a cross-sectional view of an embodiment of an improved catheter having a vent hole that only allows air to pass therethrough.

FIG. 17 is a cross sectional view of another embodiment of an improved catheter 410. The catheter 410 has one or more vent holes 440 at its distal portion. The diameter of the vent hole 440 is preferably dimensioned to be so small that flushing solution can not pass therethrough, but air can. This can be achieved, e.g., by making the vent hole 0.00005 inches in diameter. A laser, for example, may be used to make such small holes.

Figure 18:
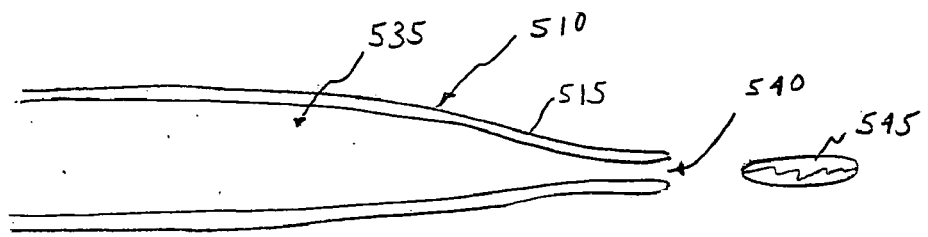
FIG. 18 is a cross-sectional view of another embodiment of an improved catheter having a vent hole and a plug.

Yet another embodiment of an improved catheter is illustrated in FIG. 18 (cross-section view). The catheter 510 includes an elongated catheter body 515 having a lumen 535 extending through the catheter body. The catheter body 510 preferably tapers down to a smaller diameter at the distal end and has a opening 540 at its distal tip. This embodiment includes a plug 545 for sealing the opening 540 after flushing. The plug 545 may be made of an elastic material, such as rubber and silicone. The plug 545 may also be made of an expanding material that expands upon contact with moisture by absorbing the moisture.

Figure 19:
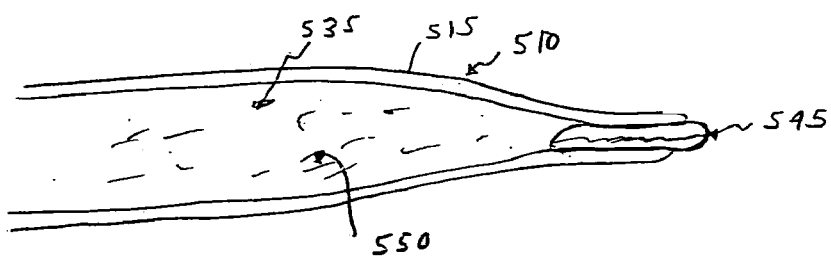
FIG. 19 is a cross-sectional view of the plug of FIG. 18 sealing the vent hole of the catheter.

To flush the catheter 510, a flushing solution is injected into the catheter lumen 535 from the proximal end of the catheter 510. The solution reaches the distal end of the catheter lumen 535 where it pushes air out through the opening 540. After the air is vented out, the plug 545 is inserted into the opening 540 to seal the opening 540, as shown in FIG. 19. For the case in which the plug 545 is made of an elastic material, the plug 545 preferably has a slightly larger diameter than the opening 540 to ensure a tight fit between the plug 545 and opening 540. For the case in which the plug 545 is made of expanding material, the plug 545 expands upon contact with the flushing solution 550, creating a tight fit between the plug 545 and the opening 540.

Figure 20A:
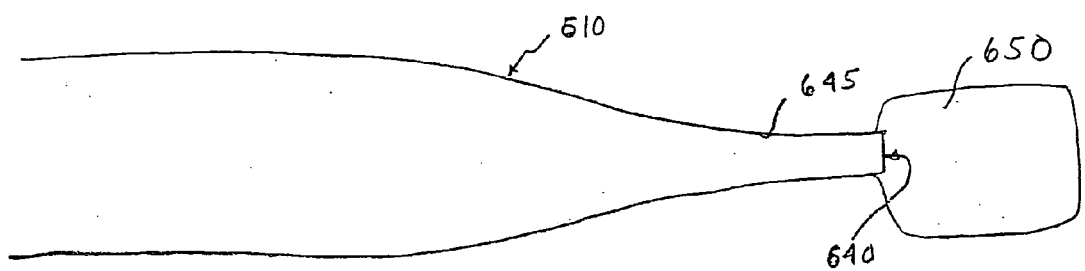
FIG. 20A is a side view.
Figure 20B:
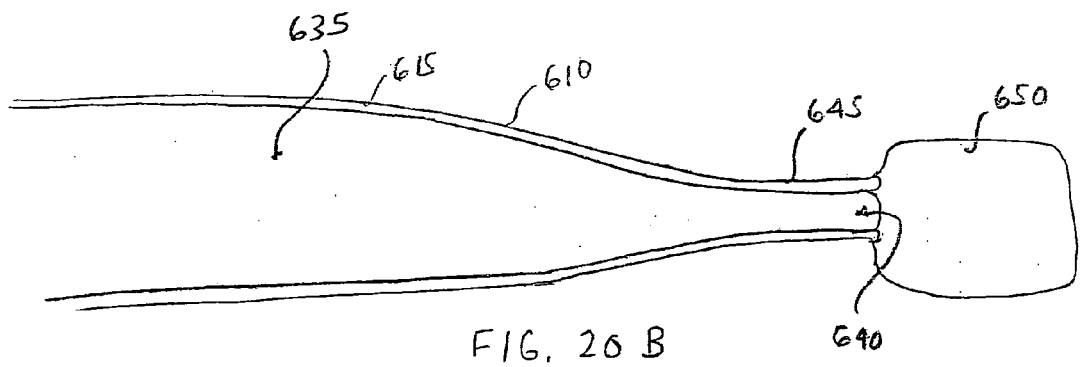
FIG. 20B is a cross-sectional view.
Figure 20C:
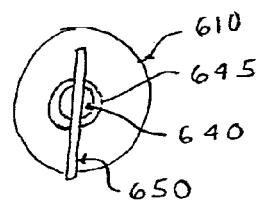
FIG. 20C is a front view of yet another embodiment of an improved catheter having a neck and a tab attached to the end of the neck.

Still another embodiment of a catheter with an air-venting apparatus is illustrated in FIG. 20A (side view), FIG. 20B (cross-section view) and FIG. 20C (front view). The catheter 610 preferably includes an elongated catheter body 615 having a lumen 635 extending through the catheter body. The catheter body 615 tapers down to a narrow neck 645 at the distal end. The end of the neck 645 has a opening 640. The catheter 610 further includes a tab 650 attached to the end of the neck 645. Although FIG. 20C shows the tab 650 aligned with the center of the opening 640, it does not have to be. The neck 645 and tab 650 may be integrally formed out of one continuous piece of a material such as soft molded plastic. Preferably, the plastic is soft enough so that a clinician can twist the neck 645 by twisting the tab 650, as explained further below.

Figure 21:
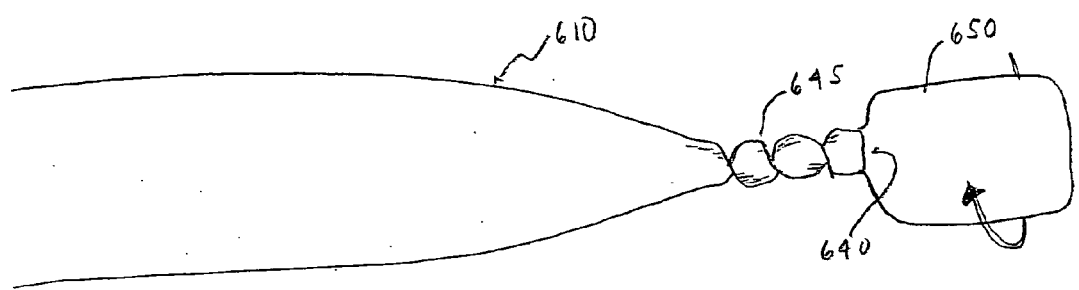
FIG. 21 shows the catheter of FIG. 20A with the neck twisted.
Figure 22:
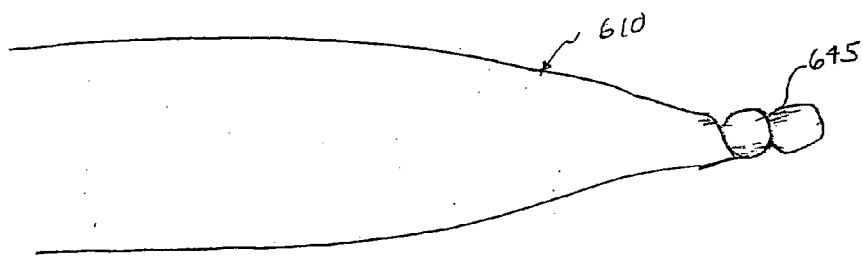
FIG. 22 shows the catheter of FIG. 21 with the tab broken off from the catheter.

To flush the catheter 610, a flushing solution is injected into the catheter lumen 635 from the proximal end of the catheter 610. The solution flows to the distal end of the catheter lumen 635 where it pushes air out through the opening 640. After the air is vented out, the neck 645 is twisted by twisting the tab 650, as shown in FIG. 21. Twisting the neck 645 causes the passage through the neck 645 to close off, thereby sealing the opening 640. Twisting the neck 645 also produces torsional stress in the neck 645 and tab 650. The stress increases as the neck 645 is twisted further. Eventually, the stress will cause the tab 650 to break off from the neck 645 or a portion of the neck 645 attached to tab 650 to break off from the rest of the neck 645, as shown in FIG. 22. In either case, the tab 650 is removed from the catheter. This way, the tab 650 does not interfere with the operation of the catheter 610 when it is guided through a body vessel.

The tab 650 may be omitted. In this case, the physician may seal the opening 640 by gripping the neck 645 with a gripping instrument (not shown) and twisting the neck 645. The gripping instrument, may be a hemostat, tweezers or the like.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As another example, each feature of one embodiment can be mixed and matched with other features shown in other embodiments. Features and processes known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A catheter, comprising:
   a catheter body having a lumen, a soft seal disposed in the lumen at a distal portion of the catheter body, an elastic cap secured to the distal end of the catheter body using an adhesive, and a vent hole disposed through the elastic cap and in communication with the lumen, wherein the diameter of the vent hole is dimensioned so that flushing solution can not pass out of the lumen through the vent hole; and
   an ultrasound imaging core received within the lumen of the catheter body.

2. The catheter of claim 1, wherein the diameter of the vent hole is approximately 0.00005-0.001 inches.

3. The catheter of claim 1, wherein the diameter of the vent hole is approximately 0.00005 inches.

4. The catheter of claim 1, wherein the lumen has a fixed diameter.

5. The catheter of claim 1, wherein the vent hole is positioned at the center of the rounded distal tip.

6. The catheter of claim 1, further comprising a flushing solution within the lumen and around the ultrasound imaging core.

7. The catheter of claim 6, wherein the flushing solution is an acoustic coupling media configured and arranged for coupling ultrasound energy between the ultrasound imaging core and a surrounding body in which the catheter is inserted.

8. A method of using the catheter of claim 1, the method comprising:
   inserting the ultrasound imaging core into the lumen of the catheter body;
   flushing the lumen of the catheter body using a flushing solution, wherein air in the lumen is vented through the vent hole; inserting the catheter into a patient body.

9. The method of claim 8, wherein flushing the lumen occurs prior to inserting the catheter into a patient body.

10. The catheter of claim 1, further comprising a seal within the lumen.

11. The catheter of claim 10, wherein the seal comprises an elastic shape-memory material.

12. The catheter of claim 1, wherein the vent hole includes at least one self-sealing vent hole that self seals upon an application of a stimulus.

13. The catheter of claim 12, wherein the stimulus is heat, pressure or moisture.

14. The catheter of claim 1, wherein the elastic cap is formed of a thermally activated shape-memory material.

15. The catheter of claim 1, wherein the elastic cap includes a second vent hole.

* * * * *